United States Patent
Light

(10) Patent No.: US 7,087,379 B2
(45) Date of Patent: Aug. 8, 2006

(54) METHOD OF DETECTING SINGLE GENE COPIES IN-SITU

(75) Inventor: Elizabeth S. Light, Gaithersburg, MD (US)

(73) Assignee: Ventana Medical Systems, Inc., Tuscan, AZ (US)

( * ) Notice: Subject to any disclaimer, the term of this patent is extended or adjusted under 35 U.S.C. 154(b) by 0 days.

(21) Appl. No.: 09/863,125

(22) Filed: May 22, 2001

(65) Prior Publication Data

US 2002/0019001 A1 Feb. 14, 2002

Related U.S. Application Data

(63) Continuation of application No. 09/419,421, filed on Oct. 15, 1999, now abandoned.

(51) Int. Cl.
*C12Q 1/68* (2006.01)
*C12M 3/00* (2006.01)
*C07H 21/04* (2006.01)

(52) U.S. Cl. ............ 435/6; 435/287.2; 536/23.1; 536/24.3; 436/94; 436/164

(58) Field of Classification Search ............ 435/5, 435/6, 69.1, 91.1, 91.2, 183, 270, 287.2; 935/77, 78; 436/94, 501, 800; 536/23.1, 536/24.3; 530/382.1

See application file for complete search history.

(56) References Cited

U.S. PATENT DOCUMENTS

| | | | |
|---|---|---|---|
| 4,935,341 A * | 6/1990 | Bargmann | 435/6 |
| 4,962,029 A | 10/1990 | Levenson et al. | |
| 5,474,916 A | 12/1995 | Reischl et al. | |
| 5,523,204 A * | 6/1996 | Singer et al. | 435/5 |
| 5,565,323 A * | 10/1996 | Parker et al. | 435/6 |
| 5,677,440 A | 10/1997 | Haralambidis et al. | |
| 5,846,728 A | 12/1998 | Haralambidis et al. | |
| 5,851,764 A | 12/1998 | Fisher et al. | |
| 6,068,843 A * | 5/2000 | Duhamel et al. | 424/184.1 |
| 6,483,641 B1 * | 11/2002 | MacAulay | 395/385 |
| 2003/0044822 A1 | 3/2003 | Fletcher et al. | |

FOREIGN PATENT DOCUMENTS

| WO | WO 94/09022 | 4/1994 |
|---|---|---|
| WO | WO 00/26415 | 5/2000 |
| WO | WO 03/025127 A2 | 3/2003 |

OTHER PUBLICATIONS

Lizard et al., "Laser scanning confocal microscopy and quantitative microscopy with a charge coupled device camera improve detection of human papillomavirus DNA revealed by fluorescence in situ hybridization", Histochemistry, (1994), vol. 101 , pp. 303-331.*

Gelmetti et al., "Detection of rabbit haemorrhagic disease virus (RHDV) by in situ hybridisation with a digoxigenin labelled RNA probe," Journal of Virological Methods, 72(1998) 219-226.*

(Continued)

*Primary Examiner*—Bradley L. Sisson
(74) *Attorney, Agent, or Firm*—Wilson, Sonsini, Goodrich & Rosati

(57) ABSTRACT

A method for detecting single copies of a gene in-situ using brightfield microscopy is used in detection of nucleic acid sequences. Probes are directly or indirectly labeled with alkaline phosphatase with NBT/BCIP used as the chromogen.

3 Claims, 3 Drawing Sheets

OTHER PUBLICATIONS

Vernole, Bio Techniques, vol. 9, No. 2, pp. 200-204.*

Davison et al., "Subtracted, Unique-Sequence, In Situ Hybridization Experimental and Diagnostic Applications," American Journal of Pathology, vol. 153, No. 5, Nov. 1998, pp. 1401-1409.*

Bains, et al, "Distribution and configuration of c-myc RNA during transcriptional attenuation in differentiating cells in-situ," Histochem Cell Biol, Springer-Verlag, p. 259-263, (1997).

Boultwood, et al, "In-Situ Analysis of Calcitonin and CGRP Expression in Medullary Thyroid Carcinoma," Clinical Endocrinology, p. 381-390, (1990).

Davison, et al, "Subtracted, Unique-Sepuence, In-Situ Hybridization," American Journal of Pathology, vol. 153 ( No. 5), p. 1401-1409, (1998).

Gelmetti, et al, "Detection of rabbit haemorrhagic disease virus (RHDV) by in situ hybridisation with a digoxigenin labelled RNA probe," Journal of Virological Methods, vol. 72, p. 219-226, (1998).

Jenkins, et al, "In-situ hybridisation of the beta-amyloid protein," Lancet, p. 1155-1156, ( Nov. 14, 1987).

Millar, et al, "Cellular localisation of messenger RNAs in rat testis: application of digoxigenin-labelled ribonucleotide probes to embedded tissue," Cell and Tissue research, Springer-Verlag, p. 269-277, (1993).

Pollice, et al, "Use of Nonradioactive DNA Probes for the Detection of Infectious Bacteria," Clinics in Laboratory Medicine, vol. 5 ( No. 3), p. 463-473, (1985).

U.S. Appl. No. 60/106,701, Fletcher et al.

Vernole, Digoxigenin-Labeled Probes Can Detect Single-Genes in Human Metaphase Chromosomes, Bio Techniques, vol. 9 (No. 2), p. 200-204, (1990).

Speel, et al, A Novel Fluorescence Detection Method for In Situ Hybridization, Based on the Alkaline Phosphate-Fast Red Reaction, Journal of Histochemistry and Cytochemistry vol. 40 (No. 9), p. 1299-1308, (1992).

Diamandis, et al, Evaluation of Non-Isoptopic Labeling a Detection Techniques for Nucleic Acid Hybridization, Journal of Clinical Laboratory Analysis, vol. 7, p. 174-179, (1993).

Linder, et al, "The ThinPrep Pap Test, A review of Clinical Studies," Acta Cytologica, vol. 41 ( No. 1), p. 30-38, ( Dec. 13, 1997).

Press, et al, "Her-2-neu Expression in Node-negative Breast Cancer: Direct Tissue Quantitation by Computerized Image Analysis and Association of Overexpression with Increased Risk of Recurrent Disease," Cancer Research, p. 4960-4970, ( Oct. 15, 1993).

Speel, et al, "A Novel Triple-color Detection Procedure for Brightfield Microscopy, Combining In Situ Hybridiztion with Immunocytochemistry," The Journal of Histochemistry and Chemistry, The Histochemical Society, Inc., vol. 42 ( No. 10), p. 1299-1307, ( Dec. 13, 1994).

Speel, et al, "Rapid Bright-Field Detection of Oligonucleotide Primed In Situ (PRINS)- Labled DNA in Chromosome Preparations and Frozen Tissue Sections," BioTechniques, vol. 20 ( No. 2), p. 226-234, ( Feb. 13, 1996).

Tanner, et al, "Chromogenic in Situ Hybridization, a Practical Alternative for Fluorescence in Situ Hybridization to Detect HER-2/neu Oncogene Amplification in Archival Breast Cancer Samples", American Journal of Pathology, vol. 157 (No. 5), p. 1467-1472), (Nov. 2000).

Zymed Laboratories, Inc., Spot-Light HER2DNA Probe, Catalog No. 84-0100, (May 17, 2001).

* cited by examiner

METHOD OF DETECTING SINGLE GENE COPIES IN-SITU

CROSS REFERENCE TO RELATED APPLICATIONS

This application is a continuation of U.S. Ser. No. 09/419,421 filed Oct. 15 1999, abandoned.

BACKGROUND TO THE INVENTION

1. Field of the Invention

The present invention relates to techniques for detection and localization of nucleic acid and, more particularly, to the use of enzyme catalyzed chromogenic compositions in such detection and localization.

2. Description of Related Art

In-situ hybridization (ISH) techniques are an important tool for detection of nucleic acid sequences, i.e., both DNA and RNA. Unique nucleic acid sequences occupy precise positions in chromosomes, cells and tissues and in-situ hybridization allows the presence, absence and/or amplification status of such sequences to be determined without major disruption of the sequences.

It is known that certain nucleic acid sequences are associated pathologic conditions in living organisms. For example, the presence of certain genes and viral nucleic acids have been implicated in precancerous and cancerous pathology. Genetic diseases are also diagnosed by determining the presence, absence or number of copies of nucleic acids. Several genetic markers have been associated with poor prognosis in patients with various cancers. Infectious microorganisms, particularly intracellular ones, contain nucleic acid sequences which are also detected to diagnose disease and monitor therapy.

Accumulation of alterations in both cellular oncogenes and tumor suppressor genes has been associated with human tumorigenesis. Gene amplification has been associated with certain aggressive forms of human cancer and has been used as a prognostic parameter in the clinical analysis of certain malignancies. Presence or absence of nucleic acid amplification can also be used to indicate treatment in certain cancers of disease states. Cellular oncogene amplification of the HER-2/neu oncogene has been shown to play an important part in the pathogenesis and prognosis of various solid tumors including breast cancer. See, e.g., Battifora et al., Modern Pathol, 4:466–474 (1991) and Press et al., Cancer Res., 53:4690–4970 (1993).

Loss and/or mutation of tumor suppressor genes is also indicative of certain cancers and certain stages of cancers. The loss of p53 is classically found in many solid tumors. In such a situation a cell usually has only one mutated copy of the gene, the other copy being lost due to aneuploidy. Loss of both copies is also found.

Human Papilloma virus (HPV) is a common sexually transmitted viral disease. There are at least 70 distinct types of HPV. Some HPV types found in genital lesions have been implicated in cervical precancers and cancers (for example, types 16, 18, 31, 33 and 35) while other types are relatively benign (Types 6, 11, 42, 43 and 44).

Currently, Pap smears are performed yearly on women to check for the presence of atypical or cancerous cells. Roughly 90% of all Pap smears are normal, 3% are unequivocally dysplastic, and 7% are squamous atypias (ASCUS) or low grade squamous intraepithelial lesions (LSIL). The ASCUS and LSIL diagnoses present the doctor and patient with multiple choices for treatment. The ability to accurately test these patients for high risk type HPV presence would provide further information on the best course of therapy. For example, the presence of a low risk HPV type may indicate no further action except perhaps more frequent Pap smears. A high risk HPV type presence would indicate a more aggressive approach.

Other viral diseases are also frequently difficult to detect or distinguish clinically. Examples include Epstein-Barr virus (EBV), cytomegalovirus (CMV), hepatitis viruses, etc. Nucleic acid based detection systems performed in-situ for these viruses is also desirable.

At least four types of nucleic acid probes are commonly used for in-situ hybridization. These include double stranded DNA (dsDNA) probes, single stranded DNA probes (ssDNA), single-stranded RNA probes (ssRNA), and oligonucleotide probes. The production and application of a large variety of DNA and RNA probes has been made possible through the availability of many molecular cloning techniques including plasmid, phage P1, cosmid, and yeast artificial chromosome (YAC) cloning procedures, cell hybrid technology, chromosome sorting and dissection techniques, and amplification techniques such as the polymerase chain reaction (PCR). Additionally, the use of DNA synthesizers can permit oligonucleotides to be custom designed and chemically synthesized. Different target sequences such as specific genomes, chromosomes, repetitive and unique sequences, microsatellites, mitochondrial nucleic acids, mRNA, or microbial (viral) nucleic acids may be identified depending on the selection of probe used in the ISH procedure. Nucleic acid probes may be labeled by conjugation to a marker to create a detectible probe hybridization site.

A variety of detection systems have been developed which are based on ligands which bind to a probe either directly or indirectly and markers or labels which allow visualization of the probe and hence, the site where the probe has hybridized. Radioactive labels or non-radioactive fluorescent labels have been employed as such markers or labels either directly linked to the probe or attached through secondary means such as antibodies. Although radioactive labels are effective, they are associated with radioactive toxicity and environmental concerns. Fluorescent non-radioactive detection protocols provide several advantages for in-situ hybridization, including easy and rapid detection, high sensitivity with low endogenous background, high resolution, multiple-target analysis with different fluorochromes, and the possibility to quantitate signal. Unfortunately, the signal generated by fluorescent markers typically fades over time. Upon exposure to light and autofluorescence of the tissue sample may mask the presence of a target signal. Additionally, the cost and availability of fluorescent microscopy equipment and trained personnel is greater than conventional brightfield microscopy.

Alternatively, enzyme systems have been used for detection of nucleic acid target sequences. Enzymes such as horseradish peroxidase or alkaline phosphatase can be chemically conjugated to proteins, antibodies, avidin, streptavidin, biotin, Fc-binding proteins such as protein A or G for use in hapten interactions, or directly to the nucleic acid probes. Certain enzymes interact with chromogen substrate solutions to produce distinctly colored products which are capable of being visualized directly through brightfield microscopy. This permits the localization of hybridization sites through enzyme precipitation reactions. Some advantages of cytochemical detection with enzymes include the stability of the precipitate, indicating permanent storage of cell preparations, and the use of a standard brightfield microscope in a setting where routine analysis is performed.

Oxidoreductases are enzymes which catalyze the oxidation of various substrates, and are well suited for the preparation of enzyme-conjugates due to their excellent stability and their ability to yield chromogenic products. Peroxidases have been widely used as a label for antibodies and ligands, such as avidin and streptavidin, in immunoassay systems. Peroxidases catalyze the hydrogen peroxide oxidation of certain electron donors by transferring electrons from the donor to the peroxide and resulting in formation of a colored product and water.

A number of different chromogens have been used with enzyme-linked immunoassays (ELISA). See, e.g., U.S. Pat. No. 4,962,029. A number of other different enzymes such as kinases and phosphatases catalyze the addition and removal of phosphate moieties. These enzymes have also been used in various immunoassays.

TMB has reportedly been used in detection of repetitive DNA sequences in Speel et al., Rapid Bright-Field Detection of Oligonucleotide Primed In-Situ (PRINS)—Labeled DNA in Chromosome Preparations and Frozen Tissue Sections, Biotechniques, 20:226–234 (February 1996). The PRINS procedure involves placing haptens at a target site using enzymes to incorporate labeled nucleotides by elongating unlabeled primers. More specifically, unlabeled DNA primer is annealed to its complementary target sequence in-situ. The primer serves as an initiation site for chain elongation using DNA polymers and fluorochrome-, biotin-, or digoxigenin-labeled nucleotides. The labeled DNA chain is then detected directly by fluorescence microscopy or indirectly by fluorochrome-conjugated avidin or antibody molecules. Speel et al. describes localization of DNA target sequences using PRINS and colored precipitates of horseradish peroxidase-diaminobenzidine (brown color), alkaline phosphatase-Fast Red (red color) and horseradish peroxidase-tetramethylbenzidine (green color). Results were evaluated using bright-field microscopy.

In Speel et al., A Novel Triple-color Detection Procedure for Bright-field Microscopy, Combining In-Situ Hybridization with Immuno Chemistry, J. Hist. Cyt., vol. 47, No. 10, pp. 1299–1307 (1994), a peroxidase-TMB product was detected using in-situ hybridization techniques. The system described by either Speel et al. publication above was used only for the detection of satellite or repetitive DNA. However, the sensitivity required for detecting such multiple copy sequences is much lower than the sensitivity required for detection of unique copy sequences. If the sensitivity of techniques using labeled nucleic acids and their detection systems can be increased to allow detection of unique copy sequences, more accurate results could be obtained for detection of such sequences in diagnosis and prognostication of cancer or other disease states.

A number of patents have proposed various colormetric determinations of hybridization. These include U.S. Pat. Nos. 5,851,764, 5,846,728, 5,525,465, 5,677,440 and 5,474,916. However, none of these were able to distinguish single gene copies in-situ.

SUMMARY OF THE INVENTION

A method of detecting a target nucleic acid sequence is provided which includes hybridizing a nucleic acid sequence to a target; associating an enzyme with the nucleic acid sequence; contacting the associated enzyme with a chromogen substrate composition thereby forming a colored precipitate (chromogenic product); and observing the location of the colored precipitate. The alkaline enzyme may be associated with the nucleic acid sequence by conjugating a hapten to a nucleotide to form a hapten conjugated nucleotide; conjugating enzyme to a binding partner of the hapten to form an enzyme conjugated binding partner; and contacting the enzyme conjugated binding partner with the hapten conjugated nucleotide to form a binding partner/hapten complex.

Visualization is typically done by brightfield microscopy (for example in in-situ hybridization), spectrophotometry (for example in solution hybridization) or by visual observation (for example in solid phase hybridization).

A composition is provided which includes nucleic acid associated with the product of an insoluble chromogen formed by the action of the enzyme, particularly a dephosphorylated product of a alkaline phosphatase and a composition containing an aqueous solution of NBT/BCIP, a salt, surfactant and buffer.

A method of detecting a nucleic acid sequence is provided which includes observing the location of the insolubilized chromogenic product associated with the nucleic acid sequence, particularly in situ.

Using such a system, single copies of target nucleotide sequences may be detected in a single cell. The method provides for counting 1–5 and greater numbers of target copies per cell. The location within a cell which harbors the target may also be determined.

A primary goal of the present invention is to quantitatively determine the number of target nucleotide sequences is such a fashion that one may determine the number of copies per cell. Clinically, the presence of more or less than two copies may be indicative of certain diseases or conditions.

DETAILED DESCRIPTION OF PREFERRED EMBODIMENTS

Figure 1:
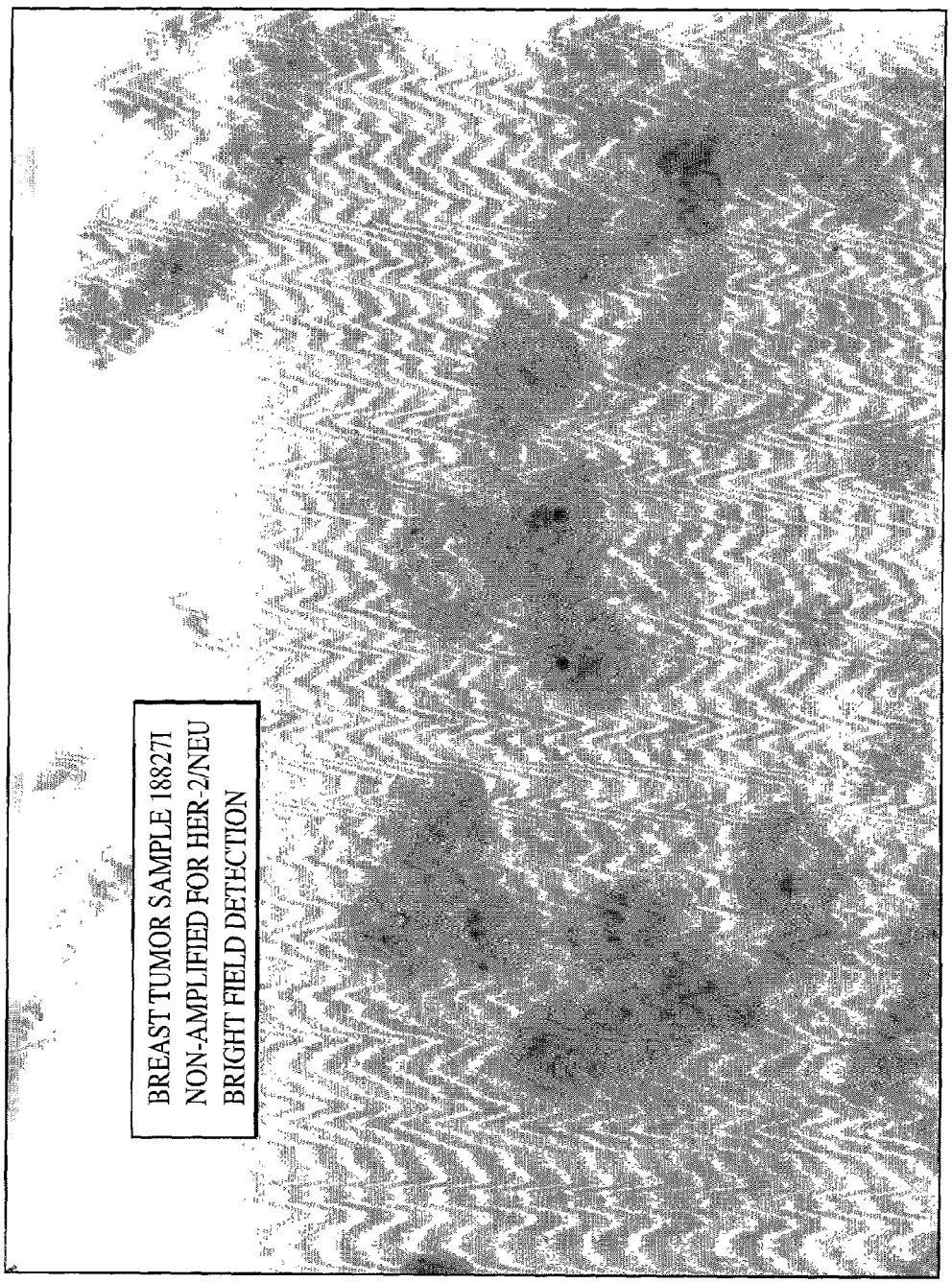
FIG. 1 depicts a microphotograph made according to the present invention using brightfield microscopy of detection of an unamplified (normal) number of HER-2/neu gene copies in cells.

By judicious selection of enzyme, chromogen and conditions, one can not only detect the presence of a nucleic acid target in a sample in-situ, but one can even count individual copies within a cell. While such has been done previously with a fluorescently or radioactively labeled probe, brightfield detection presents particular problems which has heretofore prevented counting of individual gene copies. While the signal emitted from a radioactive or fluorescent compound is inherently localized, an enzyme label is not directly observable. Rather the enzyme must convert a compound in solution into a colored compound which must not color the entire region, yet be able to be readily observable. Unlike observation of a radioactive or fluorescent signal from a dark background, under brightfield observation, cells naturally contain darkened regions. Thus, in brightfield detection, one is trapped between the limits of delectability and the formation of a spot so large that counting of individual gene copies is not possible.

Use of NBT/BCIP, salt, surfactant, and buffer provides a surprising increase in sensitivity for detection of nucleic acid sequences using alkaline phosphatase catalyzed detection techniques. Such increase in sensitivity allows detection of unique copy sequences contained within a cellular genome that were previously undetectable using TMB based reagents. It is contemplated that a NBT/BCIP composition according to the present invention can be used in any technique involving dephosphorylation and formation of a colored composition to locate a nucleic acid sequence. Such techniques include in-situ hybridization (unamplified) and primed in-situ (PRINS) labeling.

The amounts of NBT/BCIP, salt, surfactant and may be varied by routine experimentation to provide maximum solubility of each ingredient in the composition, maximum handling characteristics, e.g., viscosity, and maximum color dynamics. The amount of NBT in the final reaction may preferably range from about 200 mg/l to about 2500 mg/l, more preferably between about 500 mg/l and about 1300 mg/l and even more preferably about 830 mg/l. The amount of BCIP in the final reaction may preferably range from about 50 mg/l to about 1500 mg/l, more preferably between about 150 mg/l and about 550 mg/l and even more preferably about 287 mg/l. The amount of surfactant may preferably range from about 0.03% to about 0.001% and is more preferably about 0.015%. The concentration of magnesium chloride may range from about 0.15 M to 0.01 M, more preferably about 0.1 M to 0.06 M, most preferably about 0.08 M. The pH of the composition may be anywhere in the range which permits the enzyme to function without degrading the other reagents or solubilizing the colored product. The preferable range is from about 7 to about 11, more preferably about 9.5.

Suitable surfactants include ionic and non-ionic detergents such as dioctyl sulfosuccinate, sarkosyl, cholic acid, Triton X-100 30, Brij-35, deoxycholate, sodium dodecyl sulfate and the like. Polyhydric alcohols including propylene glycol, dipropylene glycol, 1,2,6 hexanetriol, 1,2,4 butanetriol, and the like may also be added. A preferred composition is commercially available and sold by Ventana Medical Systems, Inc., Tuscon, Ariz.

For other enzyme/chromogen combinations, the amount of TMB may preferably range from about 0.16 mg/l to about 0.28 mg/l and is more preferably about 0.22 mg/l. The amount of sodium tungstate is preferably less than about 25 ppm and more preferably less than about 1 ppm. The amount of heavy metal salt other than sodium tungstate is less than about 25 ppm and more preferably less than about 1 ppm. The amount of anionic surfactant may preferably range from about 0.06 mg/l to about 0.1 mg/l and is more preferably about 0.08 mg/l. The amount of polyhydric alcohol may preferably range from about 0.075 mg/l to about 0.125 mg/l and is more preferably about 0.1 mg/l. The amount of aprotic solvent may preferably range from about 0.18 mg/l to about 0.31 mg/l and is more preferably about 0.25 mg/l. The pH of the composition should preferably range from about 5 to about 6.5 and is more preferably about 5.67.

A preferred heavy metal salt other than sodium tungstate is cobalt salt. Suitable cobalt salts include acetate, chloride, sulfate, nitrate and the like. Suitable anionic surfactants include dioctyl sulfosuccinate, sarkosyl, cholic acid, Triton QS 30, Triton X 100, deoxycholate, sodium dodecyl sulfate and the like. Suitable polyhydric alcohols include 1,2,6 hexanetriol, 1,2,4 butanetriol and the like. Suitable aprotic solvents include dimethyl sulfoxide, dimethylformamide and the like. A preferred composition is commercially available and sold under the trade name True Blue Peroxidase Substrate by Kirkegaard & Perry Laboratories (KPL), Gaithersburg, Md.

Differing concentrations, salts, surfactants and other choices of ingredients may also be chosen by routine experimentation provided that the result is scored. With different enzyme/chromogen combinations, it is expected that some routine experimentation will be needed to sufficiently optimize the assay to become quantitative.

In general, ISH is well-known and in the present invention involves:

(1) Identification, selection, and labeling of a probe of interest. Suitable probes include oligonucleotides, plasmids, cosmids, yeast artificial chromosomes (YACS), bacterial artificial chromosomes (BACS), P1, viral sequences, etc. Examples of haptens for probe labeling include biotin, digoxigenin, dinitrophenyl, phenyloxazalone, fluorescent labels for direct or indirect labeling include fluorescein, rhodamine, coumarin, Texas Red, Rhodol Green, etc. Incorporation of the hapten-conjugated nucleotides into the nucleic acid sequence of the probe may be performed by nick translation, PCR, random priming or similar means familiar to those skilled in the art.

(2) Preparation of cells and tissue sections for ISH which routinely involves fixation and attachment of the specimen to a solid support such as a glass slide. Known procedures include formalin fixation, paraffin embedding, freezing, alcohol fixation, cutting, mounting, etc.

(3) Pretreatment of the specimens to permit penetration of the labeled nucleic acid probes and cytochemical detection molecules, or to reduce non-specific backgrounds which may be necessary for a given specimen, e.g., proteolytic digestion, RNase treatment, endogenous enzyme inactivation, etc.

(4) Heat, salts, chaotrophic agents such as formamide and/or alkaline treatment to render the double-stranded DNA probes and targets single-stranded as a prelude to, (5) hybridization, which provides the necessary conditions for the probe to bind to the target nucleic acid. A number of physiochemical conditions are known that affect hybridization, kinetics and sensitivity. Common conditions affecting rate and sensitivity of hybridization are the factors associated with stringency, especially temperature, salt concentration, chaotrophic concentration, probe length and concentration. These parameters are routinely empirically optimized by those skilled in the art.

(6) Following hybridization, postwashing to remove any nonspecific or low homology bound probe.

(7) Detecting the presence of labeled probe bound to the in-situ nucleic acid target by incubation of a color forming composition herein with a enzyme linked to, e.g., any of the following: nucleic acid probe, antibody, hapten conjugate, biotin, avidin, steptavidin, or polypeptide in any combination or order.

(8) Following detection, the specimen may be counterstained to provide color contrast with the signal color and as a means for viewing morphology of the specimen.

(9) The slide may then be made permanent by covering the specimen with a noninterferring mounting medium and a coverslip.

The ISH process has been automated with equiptment from various manufacturers. The same equiptment with appropriate changes to the processing conditions as set forth in this specification may be used for preparing slides for the present invention using quantitative brightfield detection.

It will be appreciated that for each target being detected and each different tissue type, differing concentrations and conditions will likely be required. The skilled artisan will realize this and perform routine experimentation to optimize the assay for each differing sample and target.

Various labeling techniques based on chemical or enzymatic modification of nucleic acid probe sequences may be utilized, e.g., enzymatic incorporation (e.g., nick translation, random priming), incorporation during DNA amplification (e.g. PCR) or nucleotides conjugated to haptens including biotin, digoxigenin, and dinitrophenyl. Incorporation of labeled nucleotides can also be accomplished with the primed in-situ (PRINS) technique which utilizes an oligonucleotide primer for chain elongation catalyzed by a DNA polymerase or RNA reverse transcriptase.

After hybridization of the probe containing one or more hapten conjugated nucleotides to a target nucleic acid sequence or after generation of a nucleic acid strand incorporating one or more hapten conjugated nucleotide which is complementary to one strand of the target nucleic acid sequence by PRINS, an enzyme is then associated with the target nucleic acid either directly or indirectly. Thus, when either the probe or the PRINS generated strand duplexes with the target sequence, the incorporated hapten is available for complexation with a binding partner. Typically, a binding partner of the hapten is conjugated to the oxidizing enzyme such as peroxidase. Binding partners include polypeptides, antibodies, avidin, streptavidin and biotin. Alternatively, an oxidizing enzyme can be conjugated directly to the probe or PRINS generated complementary strand.

After association of the target nucleic acid sequence with the oxidizing enzyme, the specimen is contacted with a composition including, color forming compound, salts and surfactant in accordance with the present invention. The enzyme catalyzes the composition including the color forming compound to provide an insoluble colored composition, which, after optional counterstaining, can be viewed with a brightfield microscope.

Sample preparation is important to obtaining successful results. Because the probe/antibody/enzyme complex or individual components are relatively large, the cell must be adequately digested to permit the reagents to associate at the location of the chromosome. However, over digestion is equally problematic as the cell boundaries are unclear making the counting of spots/cell difficult. Maintaining cellular morphology is also important for proper visualization.

In order to count discrete spots of precipitated colored compound, the type and amount of enzyme label and chromogen is particularly important. Certain chromogens will not be sufficiently localized to form discrete spots. For measuring genomic DNA, usually two copies and no more than four copies (just before cell division) of any so called "single copy" gene are normally present. The present invention produces spots sufficiently small that at least five copies of any target may be visualized in a cell. Larger numbers of target may merge together and still provide adequate identification that this cell is abnormal. The present invention is designed so that there is a one to one correlation between spots and copies of the target sequence at a normal copy number.

It is also contemplated that a NBT/BCIP or other chromogen composition according to the present invention can be used for signal amplification techniques well-known in the art. For example, multiple binding sites allow multiple alkaline phosphatase or other enzyme molecules to be associated with a target nucleic acid thus creating a network of alkaline phosphatase sites. In this manner, an antibody having multiple binding sites can be conjugated to a nucleotide associated with a target nucleic acid sequence. Multiple binding partners conjugated to alkaline phosphatase will then associate with the multiple binding sites of the antibody to provide multiple alkaline phosphatase enzyme molecules. Other techniques for signal amplification are well-known as well. Thus, multiple alkaline phosphatase sites will increase efficiency of dephosphorylation of NBT/BCIP composition according to the present invention.

While the invention's best mode is exemplified by using the combination of alkaline phosphatase and NBT/BCIP, which gave the best quantitative results, the following combinations have also been found to be operable by experimental data in ISH.

Horseradish peroxidase as the enzyme and 3,3',5,5' tetramethylbenzidine as the color forming compound in a composition containing, sodium tungstate and a heavy metal salt other than sodium tungstate, anionic surfactant, polyhydric alcohol and aprotic solvent has been used to detect single gene copies in-situ. Also, horseradish peroxidase as the enzyme with diaminobenzidine as the color forming compound has been used to detetct single gene copies in-situ.

It will be appreciated that other enzyme and chromogen combinations may be used. Suitable lists of possible enzyme and chromogen combinations are known from the immunoassay field, particularly in immunohistochemistry. Common examples include horseradish peroxidase and AEC or any of a number of benzidine and napthol based compounds. Any of the enzyme chromogen combinations may be amplified using any of the tyramide based systems known per se. Likewise, enzyme and chromogen compositions may be optimized using similar reagents and conditions as have been used in such immunoassays.

However, unlike immunohistochemistry, single copies of nucleic acids are being detected with ISH. In immunohistochemistry, one is almost never detecting a single molecule of protein and certainly cannot count individual molecules in a multi protein molecule per cell sample. Thus one cannot directly utilize any enzyme/chromogen combination from immunohistochemistry without first altering the assay in a manner in accordance with the present invention to generate a quantitative ISH.

While described for in-situ detection, the present invention may be used to determine the presence of nucleic acid sequences in other environments as well such as extracted DNA and RNA for any hybridization assays such as Southern, Northern, dot and reverse dot blots.

Levels of mRNA may be detected and even quantified by using the labeling and detection system of the present invention. This detection may be performed in-situ or by extracted RNA or its cDNA.

The gene HER-2/neu gene is amplified in a number of cancers including breast, prostate, ovarian, endometrial and colorectal. In each situation, it is important to determine the approximate number of gene copies in each cell. Knowing an average number is unacceptable as a few cancer cells in a small metastasis in a sample of mostly normal cells may have "on average" a "normal" number. Thus, the importance of counting the gene copy number within a single cell.

Localization of a target nucleotide sequence within a single cell can determine whether the target is within the nucleus, mitochondria or associated with a structure (e.g. the rough endoplasmic reticulum) in the cytoplasm. This is a different localization from what has been referred to in the prior art. The present invention is detecting a spot localized in a cell, not a cell or group of cells in a tissue.

In addition to the numerous uses stated above for an in-situ assay detecting individual gene copies in a cell, the present invention may be used for all genetic testing, including prenatal testing of amniotic fluid, CVS, fetal cells in maternal blood, etc. Genetic testing has uses beyond disease diagnosis, such as compatibility and tissue typing for blood, tissue and organ transplantation, monitoring bone marrow transplants, paternity, forensic and archeological testing. Perhaps the best known example of disease associated with extra copies of a nucleic acid is Down's Syndrome which is detectable by having an extra chromosome 21.

The detection of individual copies of target nucleic acid sequences permits one to detect aneuploidy, microsatellite instability, lengths of repeats (such as in severity of Fragile X determination), susceptibility to cancer or other diseases and heterozygosity of any gene.

While detecting individual target copies of an infectious microorganism may not always be necessary, the infection of a virus and its replication may be observed and quantified using the present invention. For example, HIV, HSV, CMV, T. palidium, M. tuberculosis, etc. Furthermore, microorganisms may be in a latent or repressed state in very low copy numbers such that a single gene copy per cell may be all that is present. Microorganisms which integrate into the host cell chromosome may have only one copy per cell present. Thus the great sensitivity of the present invention is preferred.

One may use multiple probes, each labeled with the same or different enzymes or haptens for associating an enzyme with the probe. Such arrangements would permit detection of multiple target sequences simultaneously. This may further characterize a particular disease state or detect plural diseases simultaneously. This variation is particularly useful when the ratio of one target sequence to another target sequence is relevant. By using different chromogens, different colored spots may be formed which can be visualized and counted.

Unlike previous methods of in-situ detection, clinical testing, particularly automated clinical testing involves biological samples from a wide variety of fluids and tissues. A method for detection of individual nucleic acid copies in a cell under such diverse conditions requires a flexible and superior detection system. The present invention has achieved such a result in an automated format.

The following examples are included for purposes of illustrating certain aspects of the invention and should not be constructed as limiting.

EXAMPLE 1

HER-2/neu Brightfield Assay for Embedded Breast Tissue Specimens

Paraffin embedded tissue specimen slides were baked for 1 to 20 hours at 65° C. +/−2° C. The slides were then deparaffinized in three washes of xylene for 5 minutes each and washed in 100% ethanol, 2 times for 2 minutes each and air dried label end down, propped at an angle.

Next, the specimens were digested in 0.5 mg/ml Proteinase K/2×SSC (pH 7.0) at 45° C. (Proteinase K solution was prepared by adding 1 ml deionized water to a 25 mg vial of Proteinase K, shaking the vial to suspend the Proteinase K and transferring the 1 ml of solution to 50 ml of 0×SSC prewarmed to 45° C.). Cell line controls were digested for 12 minutes, and tissue specimens for 35 minutes. The slides were rinsed for 10 seconds in 2×SSC at room temperature followed by dehydration in a room temperature ethanol series of 70%, 80%, and 100% ethanol for 1 minute each. The slides were air dried with the label end down.

10 μl digoxigenin-labeled probe, prewarmed to 37° C. for 5 minutes, was added to each specimen. The slide was then heated at 90° Celsius for 12 minutes (for example, in an MJ Research thermocycler with a slide block) to denature probe and target DNA. The slide was coverslipped and transferred to a prewarmed humid chamber and hybridized for 4 hours to overnight at 37° C.

The glass coverslip was removed and the slide washed in a Coplin jar containing prewarmed 1×SSC for 5 minutes at 72° C. The slides were transferred to a coplin jar of room temperature wash solution of a detergent and a buffer for example, Tris buffer and Brij-35 (APK wash solution, Ventana Medical Systems, Inc.

Anti-digoxigenin Alkaline Phosphatase (Boehringer Mannheim Cat. 1093274) was diluted 1:150 in 100 mM Tris pH 7.5/150 mM NaCl. 100 μl of the diluted antibody was added to each slide, covered with a plastic coverslip, and incubated for 30 minutes at 37° C. in a humid chamber. The slides were then washed in a 10-second stream of APK and transferred to a Coplin jar of APK until all slides are washed.

While the slides drain, a magnesium chloride solution (Ventana Enhancer 1:4) (100 ul+300 ul) with APK was prepared. 400 ul was added to each slide, the slides placed on the Lab-Line Orbit Shaker at room temperature and shaken at 1000 rpm for 4 minutes.

Ventana NBT (6×NBT) was mixed 1:1 with Ventana Blue BCIP (6×BCIP) (100 ul+100 ul). 200 ul of the mixture was added to the puddle of solution on each slide and shaking continued for 30–60 minutes. This shaking was stopped when the reagent pool starts to darken or the development looks complete when viewed with the scope. Each slide was washed in a 10-second stream of deionized water from a squirt bottle and transferred to a Coplin jar containing deionized water. The deionized water was changed and incubated for 1 minute at room temperature.

To enhance visualization, the slides were counterstained by draining the slides well and added to a Coplin jar containing 1×KPL Eosin (Cat.71-02-00), diluted from stock in deionized water. Incubation was for 20 seconds at room temperature. Each slide was washed in a 10-second stream of deionized water from a squirt bottle and transferred to a Coplin jar containing deionized water. Deionized water was changed and incubated 60 seconds at room temperature.

The slides were dried in ethanol quickly by dipping them in Coplin jars containing 70%, 80% and 100% ethanol. The slides were removed and air dried. For long term storage, the slides were soaked in xylene, and a drop of Permount and a coverslip were added.

EXAMPLE 2

Detection of Single Gene Copies

The slides produced in Example 1 were mounted with Permount (Fisher Scientific, NJ) and coverslipped.

Using brightfield microscopy, microphotographs were made on Kodak Ektachrome color slide film (EL 400), using a Zeiss Axiophot 20 epi-fluorescence microscope (Zeiss, West Germany) equipped with a 100×Plan-Neofluar oil immersion objective or a 100×Plan-APO oil immersion objection (Zeiss, West Germany), a Zeiss MC-100 camera (Zeiss, West Germany), and a blue or neutral density filter.

Figure 2:
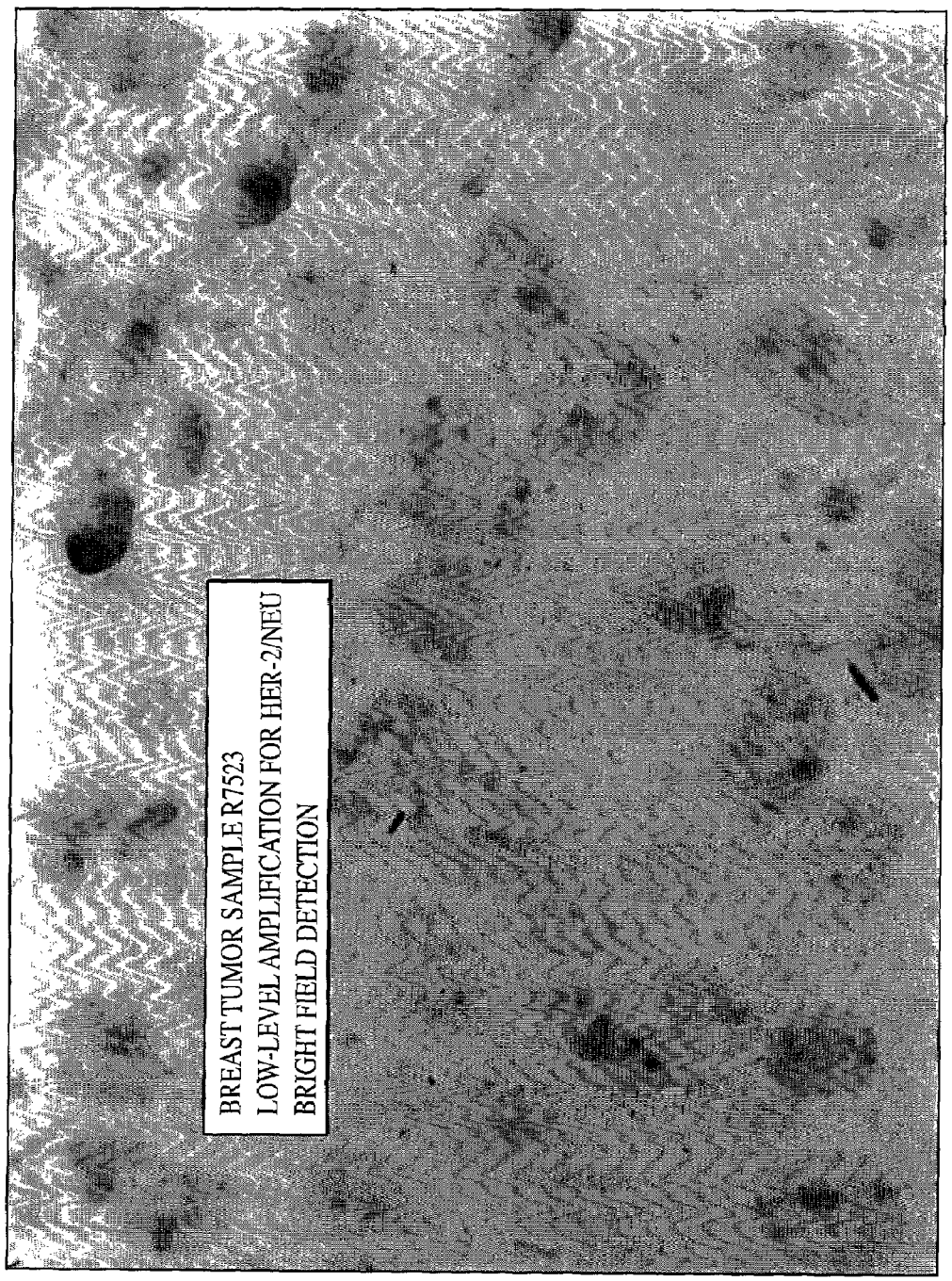
FIG. 2 depicts a microphotograph made according to the present invention using brightfield microscopy of detection of a low amplified number of HER-2/neu gene copies in cells.
Figure 3:
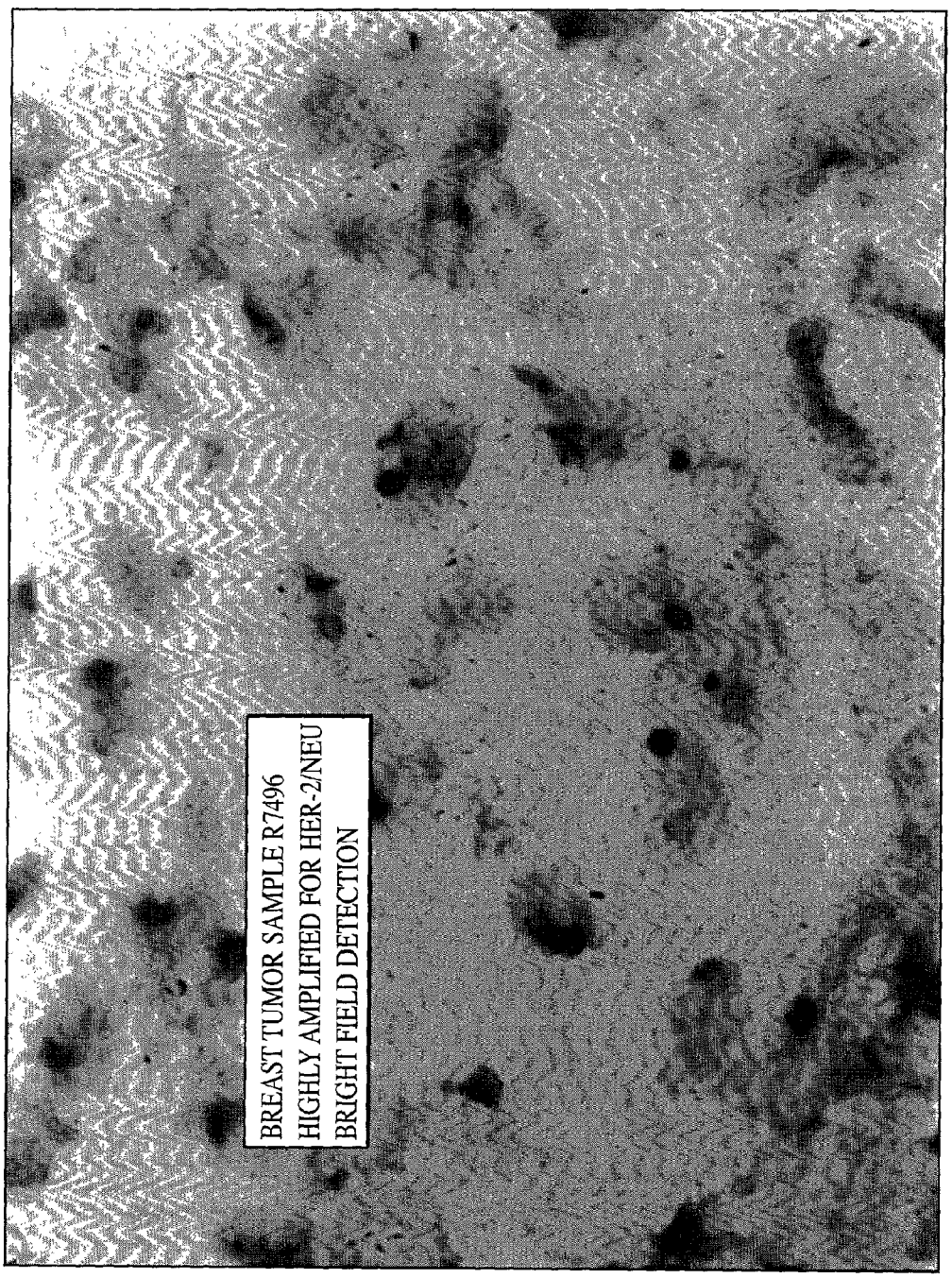
FIG. 3 depicts a microphotograph made according to the present invention using brightfield microscopy of detection of a high amplified number of HER-2/neu gene copies in cells.

As can be seen from FIGS. 1, 2 and 3 single blue signal was visible at the location of each copy of the HER-2/neu gene. The expected results for visualization of the HER-2/ neu gene in normal metaphase chromosomes from the MDA-MB468 breast tumor cell line is two; one on each chromatin, and the number of the blue signals in normal interphase nuclei is also two, or possibly two pairs if the cell is in G2 phase. In the cultured breast tumor cell lines MDA-MB-361 and SK-BR-3, multiple blue signals are visible in both metaphase chromosomes and interphase nuclei, indicating presence of multiple copies of the HER-2/neu gene. The cell nuclei and chromosomes were stained light pink for color contrast.

EXAMPLE 3

Detection of High Risk Human Papilloma Virus in Gynecologic Tissue Specimen

Six separate commercially available plasmids, i.e., pGem2, pUC13, pGem1, pLINK322, pGEM1 and pUCI3 containing entire genomes of HPV types 16 (DNA sequence available from GenBank, Accession No. K02718), 18 (DNA sequence available from GenBank, Accession No. X05015), 31 (DNA sequence available from GenBank, Accession No. J04353), 33 (DNA sequence available from GenBank, Accession No. M12732), 35 (DNA sequence available from GenBank, Accession No. M74117) and 51 (DNA sequence available from GenBank, Accession No. M62877) respectively, were labeled by nick translation with digoxigenin dCTP. Alternatively, one may clone the HPV into a plasmid by standard molecular biology techniques within the skill of the art. The labeled plasmids were then mixed together to form a single reagent. Incorporation of the digoxigenin nucleotide into the labeled DNA was verified by dot-blot procedure. DNA fragment size was determined by gel electrophoresis and was ideally between 100 and 200 base pairs.

Uterine cervix cells were sampled and smeared to form a conventional Pap smear or suspended in PreservCyt (Cytyc Corporation), a buffered fixative and preservative solution. The ThinPrep 2000 (Cytyc Corporation) was used in make two ThinPrep slides for each patient. See Linder et al., The ThinPrep Pap Test, A Review of Clinical Studies, Acta Cytologica, Vol. 41, No. 1, pp. 30–38 (1997) herein incorporated by reference. One slide was stained for conventional cytology similar to that of conventional PAP smears and the other slide was prepared as below.

The Pap smear and the ThinPrep slide were incubated for 20 minutes at 37° C. in a solution of 10 micrograms per milliliter of Proteinase K in 2×SSC. Following the incubation, the slides were washed for 2 minutes at room temperature in 2×SSC, dehydrated in a series of 70%, 80%, and 95% room temperature ethanol solutions for 1 minute each and air dried.

A probe solution was made using the above probes consisting of 0.5 microgram per milliliter of HPV types 18, 33, 35, and 51 and 0.2 micrograms per milliliter of HPV types 16 and 31 in Hybrisol VII (Oncor, Gaithersburg, Md.). Ten microliters of this probe solution was pipetted onto the ThinPrep sample slide and the specimen was covered with a 22 mm round coverslip and sealed with rubber cement. The slide was placed on a prewarmed 75° C. hot plate for 5 minutes to denature the probe and target DNA and then transferred to a humidified chamber and placed in a 37° C. incubator.

The slide was incubated at 37° C. in the humidified chamber for 2 to 16 hours to hybridize.

After the 37° incubation for hybridization, the rubber cement and coverslip was removed. The slide was washed for 5 minutes at 72° C. in prewarmed 2×SSC. The slide was then transferred to a coplin jar at room temperature containing 1×PBD (phosphate buffered detergent) for approximately 2 minutes to equilibrate.

Both high stringency post hybridization wash conditions (0.2×SSC, 2% BSA, 60° C., 10 minutes) and low stringency post hybridization wash conditions (2×SSC, 2% BSA, 45° C., 10 minutes) were used on a number of patient samples for whom the HPV type was determined.

The sample is incubated for 30 minutes at 37° C. with 100 µl of alkaline phosphatase (AP) labeled anti-digoxigenin antibody (Boehringer Mannheim GMBH) diluted 1:150 in 100 mM Tris pH 7.5/150 mM NaCl. The slide is washed three times for ten seconds using APK wash solution to remove any unbound or loosely bound antibody.

The slide is removed and allowed to drain briefly. Four hundred microliters of Ventana Enhancer is added to the slide and the reaction proceeded at room temperature for 30–60 minutes while shaking. The slides are rinsed in distilled water and allowed to air dry.

The slide is dipped in a 1/4×solution of Eosin in ethanol to counterstain. The slide is rinsed three times in distilled water and allowed to air dry. To mount, the slide is dipped in xylene and a drop of Permount (Fisher) is added. The slide is then covered with a 22 mm round glass coverslip.

Using brightfield microscopy, microphotographs are made on Kodak Ektachrome color slide film (EL 400), using a Zeiss Axiophot 20 epi-fluorescence microscope (Zeiss, West Germany) equipped with a 100×Plan-Neofluar oil immersion objective or a 100×Plan-APO oil immersion objection (Zeiss, West Germany), a Zeiss MC-100 camera (Zeiss, West Germany), and a blue and/or neutral density filter.

Cells infected with HPV integration demonstrate a blue precipitate in the nuclei with minimal slide background. The cytoplasm is counterstained pink for contrast. Cellular morphology confirmed that HPV was present in abnormal cells; normal cells do not exhibit a positive signal.

A sizable number of normal, ASCUS and SIL PAP smears are tested for HPV type status. Those detected by the probe reagent of the present invention are indicated as positive cases. The probes above are also tested against three known cell lines having different copy numbers of HPV to confirm the ability to detect HPV with respect to the copy number of viruses in each cell line.

EXAMPLE 4

Automated ISH Staining and Single Gene Copy Detection

The paraffin-embedd method of Example 1 was repeated on a DISCOVERY™ automated slide stainer discribed in PCT/US99/04181 with all steps being performed automatically. Using the same reagents and conditions of Example 1, individual spots representing single gene copies were observed using the detection methods of Example 2.

Therefore, the above description should not be construed as limiting, but merely as exemplifications of preferred embodiments. Those skilled in the art will envision other modifications within the scope and spirit of the following claims.

What is claimed is:

1. A method of visually detecting a single copy of the Her-2/neu gene in chromosomal DNA in an intact cell using brightfield microscopy, comprising:

heating the tissue or cell sample sufficiently to dissociate the native chromosomal target strands of Her-2/neu DNA;

contacting said tissue or cell sample with a digoxigenin-labeled nucleic acid Her-2/neu probe specific for the Her-2/neu gene under conditions that allow the re-hybridization of the labeled nucleic acid Her-2/neu probe and target strands of Her-2/neu DNA to form a target-probe duplex;

contacting the target-probe duplex with an anti-digoxigenin antibody under conditions allowing the antibody to bind to the label;

contacting the anti-digoxigenin antibody with an enzyme and a chromogen composition under conditions allowing the development of a visually detectable chromogen substrate signal at each target-probe duplex in the nucleus of the intact cell separate and distinct from the chromogenic signals of other copies of said chromosomal target nucleic acid sequence; and detecting the chromogenic substrate signal visually using brightfield microscope conditions.

2. The method of claim 1 wherein the enzyme is selected from the group consisting of a phosphatase and a peroxidase.

3. The method of claim 1 wherein the chromogen is selected from the group consisting of NBT/BCIP, tetramethylbenzidine and diamino benzidine.

* * * * *

UNITED STATES PATENT AND TRADEMARK OFFICE
CERTIFICATE OF CORRECTION

PATENT NO. : 7,087,379 B2 Page 1 of 1
APPLICATION NO. : 09/863125
DATED : May 22, 2001
INVENTOR(S) : Elizabeth S. Light It is certified that error appears in the above-identified patent and that said Letters Patent is hereby corrected as shown below:

Column 12, line 66, after "intact cell," please insert --in a tissue sample--.

Column 13, line 1, after "heating the tissue", please delete "or cell".

Column 13, line 2 and 3, after "Her-2/neu DNA;", please insert --enzymatically digesting the tissue in the tissue sample;--.

Column 13, line 4, after "contacting," please delete "said" and insert --the-- and after "tissue", please delete "or cell".

Column 14, line 2, after "duplex", please insert --in the nucleus of the cell in the tissue sample--.

Column 14, line 3, after "nucleus of the", please delete "intact".

Column 14, line 3, after "cell", please insert --in the tissue sample--.

Column 14, line 4, after "other copies of", please delete "said chromosomal target nucleic acid sequence" and insert --the Her-2/neu gene--.

Signed and Sealed this

Twenty-sixth Day of December, 2006

JON W. DUDAS
*Director of the United States Patent and Trademark Office*

UNITED STATES PATENT AND TRADEMARK OFFICE
CERTIFICATE OF CORRECTION

PATENT NO. : 7,087,379 B2  Page 1 of 1
APPLICATION NO. : 09/863125
DATED : August 8, 2006
INVENTOR(S) : Elizabeth S. Light It is certified that error appears in the above-identified patent and that said Letters Patent is hereby corrected as shown below:

Column 12, line 66, after "intact cell," please insert --in a tissue sample--.

Column 13, line 1, after "heating the tissue", please delete "or cell".

Column 13, line 2 and 3, after "Her-2/neu DNA;", please insert --enzymatically digesting the tissue in the tissue sample;--.

Column 13, line 4, after "contacting," please delete "said" and insert --the-- and after "tissue", please delete "or cell".

Column 14, line 2, after "duplex", please insert --in the nucleus of the cell in the tissue sample--.

Column 14, line 3, after "nucleus of the", please delete "intact".

Column 14, line 3, after "cell", please insert --in the tissue sample--.

Column 14, line 4, after "other copies of", please delete "said chromosomal target nucleic acid sequence" and insert --the Her-2/neu gene--.

This certificate supersedes Certificate of Correction issued December 26, 2006.

Signed and Sealed this

Thirtieth Day of January, 2007

JON W. DUDAS
*Director of the United States Patent and Trademark Office*